US011957452B2

(12) United States Patent
Pyne

(10) Patent No.: US 11,957,452 B2
(45) Date of Patent: Apr. 16, 2024

(54) ENHANCED GONIOMETER

(71) Applicant: PMotion, Inc., New York, NY (US)

(72) Inventor: Keith Pyne, New York, NY (US)

(73) Assignee: PMotion, Inc., New York, NY (US)

( * ) Notice: Subject to any disclaimer, the term of this patent is extended or adjusted under 35 U.S.C. 154(b) by 120 days.

(21) Appl. No.: 17/342,959

(22) Filed: Jun. 9, 2021

(65) Prior Publication Data

US 2021/0386323 A1    Dec. 16, 2021

Related U.S. Application Data

(60) Provisional application No. 63/037,218, filed on Jun. 10, 2020.

(51) Int. Cl.
*A61B 5/107* (2006.01)
*A61B 5/00* (2006.01)

(52) U.S. Cl.
CPC ............ *A61B 5/1071* (2013.01); *A61B 5/742* (2013.01); *A61B 5/7475* (2013.01); *A61B 5/6898* (2013.01)

(58) Field of Classification Search
None
See application file for complete search history.

(56) References Cited

U.S. PATENT DOCUMENTS

| | | | |
|---|---|---|---|
| 2005/0256673 A1 | 11/2005 | Hikida et al. | |
| 2008/0312549 A1* | 12/2008 | Levin | A61B 5/1121 600/546 |
| 2010/0161271 A1 | 6/2010 | Shah et al. | |
| 2012/0220904 A1* | 8/2012 | Warren | G01B 9/10 600/595 |
| 2012/0232431 A1* | 9/2012 | Hudson | A61B 5/1071 600/595 |
| 2013/0041617 A1* | 2/2013 | Pease | A43B 3/34 702/139 |
| 2013/0265225 A1 | 10/2013 | Nasiri et al. | |
| 2015/0045700 A1* | 2/2015 | Cavanagh | G16H 40/67 600/595 |
| 2015/0332004 A1* | 11/2015 | Najafi | G16H 50/20 706/46 |

(Continued)

FOREIGN PATENT DOCUMENTS

WO    WO 2020073100 A1    4/2020

OTHER PUBLICATIONS

Ferriero et al., "Reliability of a smartphone-based goniometer for knee joint goniometry", International Journal of Rehabilitation Research, 2013, 36(2):146-151.

(Continued)

*Primary Examiner* — Benjamin S Melhus
(74) *Attorney, Agent, or Firm* — Fish & Richardson P.C.

(57) ABSTRACT

Methods, systems, and apparatus, including computer programs encoded on computer-storage media, for an enhanced goniometer. In some implementations, a method includes obtaining a sequence of measurements to be measured based on one or more data points of an examination; receiving input from a user initiating a measurement; receiving raw data from a measuring component; processing the raw data to exclude measurements corresponding to one or more axes; generating a measurement result based on the processed raw data; and providing the measurement result for output.

21 Claims, 6 Drawing Sheets

(56) References Cited

U.S. PATENT DOCUMENTS

| | | | |
|---|---|---|---|
| 2016/0073931 A1 | 3/2016 | Ferber et al. | |
| 2016/0081594 A1 | 3/2016 | Gaddipati et al. | |
| 2016/0220175 A1* | 8/2016 | Tam | A61B 5/4528 |
| 2016/0324461 A1* | 11/2016 | Hallberg | A61B 5/1121 |
| 2017/0086751 A1* | 3/2017 | Amos | A61B 5/224 |
| 2017/0238849 A1* | 8/2017 | Chapman | A61B 5/6832 |
| 2019/0038187 A1* | 2/2019 | Latella, Jr. | G06F 3/0346 |
| 2019/0059788 A1* | 2/2019 | Warren | G01B 7/30 |
| 2019/0117128 A1 | 4/2019 | Chen et al. | |
| 2020/0008745 A1* | 1/2020 | Burch, V | G16H 50/30 |
| 2020/0093383 A1* | 3/2020 | Arkans | A61B 5/4836 |
| 2020/0375496 A1 | 12/2020 | Nino et al. | |
| 2021/0022666 A1* | 1/2021 | Malawey | A43B 17/006 |
| 2021/0059614 A1* | 3/2021 | Hiyama | A61B 5/7246 |
| 2021/0076981 A1* | 3/2021 | Hacking | A61B 5/6801 |
| 2021/0236020 A1* | 8/2021 | Matijevich | A61B 5/7455 |
| 2021/0315323 A1* | 10/2021 | Hakkala | A61B 5/107 |
| 2022/0218233 A1* | 7/2022 | Huang | A61B 5/1171 |
| 2022/0338759 A1* | 10/2022 | Vidal | A61B 5/7242 |
| 2023/0034341 A1* | 2/2023 | Huang | A61B 5/7264 |

OTHER PUBLICATIONS

PCT International Search Report and Written Opinion in International Appln. No. PCT/US2021/036607, dated Sep. 29, 2021, 7 pages.

International Preliminary Report on Patentability in International Appln. No. PCT/US2021/036607, dated Dec. 22, 2022, 6 pages.

Balsalobre-Fernandez et al., "Concurrent validity and reliability of an iPhone app for the measurement of ankle dorsiflexion and inter-limb asymmetries iPhone," Journal of Sports Sciences, Jul. 2, 2018, 37(3):249-253.

Extended Search Report in European Appln. No. 21820826.2, dated Feb. 7, 2024, 9 pages.

Otter et al., "The reliability of a smartphone goniometer application compared with a traditional goniometer for measuring first metatarsophalangeal joint dorsiflexion," Journal of Foot and Ankle Research, Jul. 23, 2015, 8:30, 7 pages.

* cited by examiner

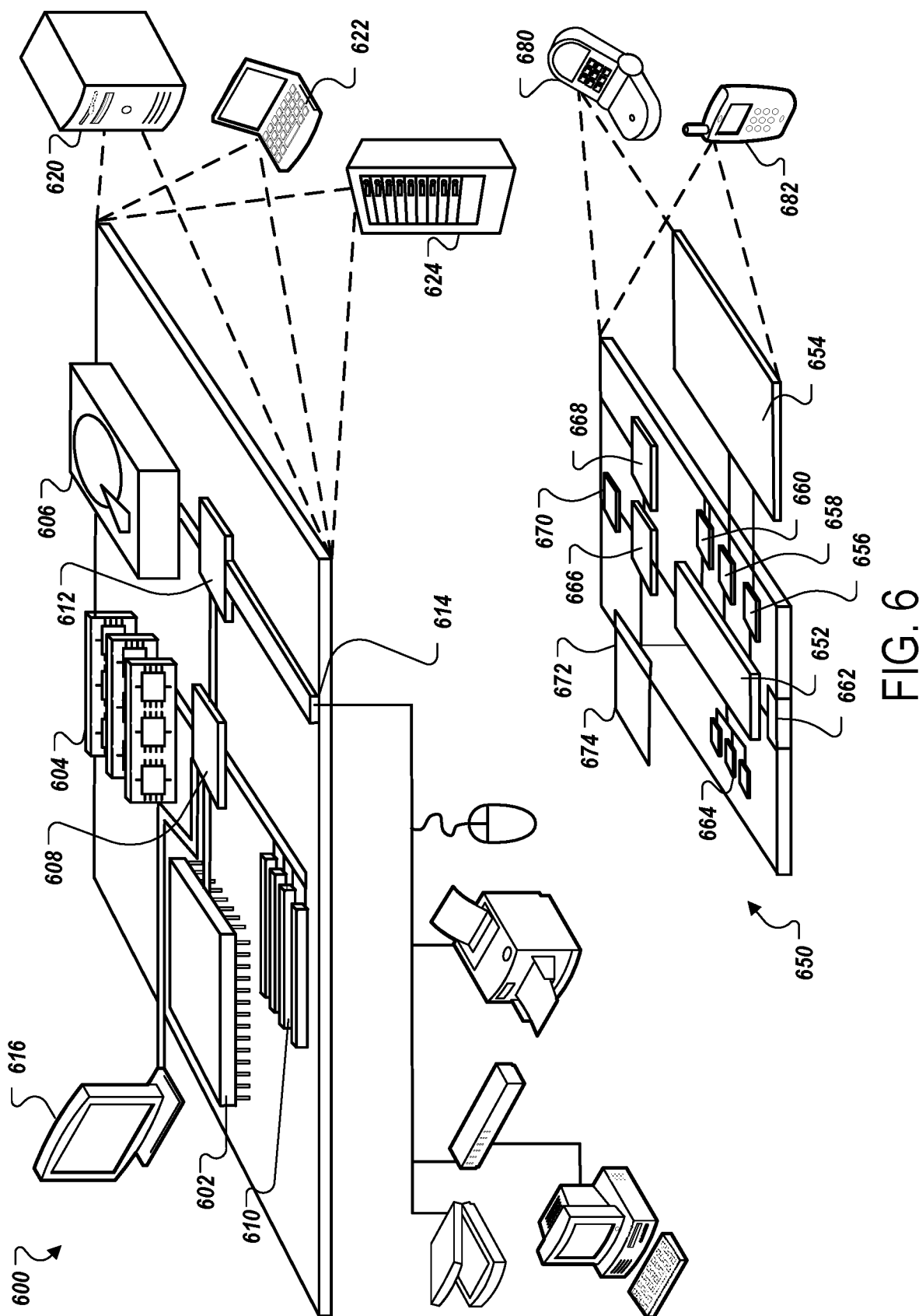

ENHANCED GONIOMETER

TECHNICAL FIELD

This specification generally describes an enhanced goniometer.

BACKGROUND

A goniometer is an instrument that is used for the precise measurement of angles. A physician or physical therapist can, for example, use a goniometer to measure an angular range of motion of a patients joint.

Currently, many companies, e.g., sports organizations, have incorporated wellness programs aimed at reducing lifestyle markers such as high blood pressure, cholesterol levels, hemoglobin A1c (HA1c) and weight. Devices worn by employees, executives, and athletes allow companies to track data such as sleep patterns, daily steps, heart rate training, or respiration rate.

In the world of sports, keeping athletes on the field is pertinent to the overall organizational success. Many of the same wellness strategies that have been used by sports organizations have been incorporated in the corporate world, leading to a robust, data driven approach for tracking and using certain key data variables.

SUMMARY

In some implementations, an enhanced goniometer of the present disclosure may be used to measure a movement of a patient. For example, in order to accurately measure the movement, the enhanced goniometer may select, based on the particular movement, one or more axes about which an angle is to be measured. The goniometer may then disable angle measurements corresponding to the axes not selected and inform a user to proceed in measuring the movement. By isolating angle measurements to only angles of interest for a particular measurement of movement, the enhanced goniometer may improve the accuracy of angle measurements and thereby improve resulting diagnoses.

In some implementations, the enhanced goniometer may selectively filter or disable one or more axes of measurement. For example, the enhanced goniometer may receive data measurements from an application programing interface (API) and select one or more of the data measurements from the API to calculate an angle in regard to a specified axis for a specified measurement.

In some implementations, the enhanced goniometer may measure an angle measurement based on one or more other angle measurements. For example, a device of an enhanced goniometer may be situated at a specific angle in relation to a first axis. Based on the specific angle in relation to the first axis, the enhanced goniometer may determine one or more other angles, measured with respect to one or more other axes, in order to determine an angle with respect to the first axis.

In some implementations, an enhanced goniometer of this specification is used within a Movement Analytic Performance System (MAPS), which is a data-driven injury prevention and correction system. The enhanced goniometer may be used to capture biomechanical, qualitative, and quantitative data as well as to help determine medical biomarkers. The enhanced goniometer may also be used to aid in tracking and ultimately predicting and treating musculoskeletal injuries.

In some implementations, an enhanced goniometer of this specification is used in a specific biomechanical exam. For example, a biomechanical exam can include measurements of limbs or other parts of the body with a goal of collecting pertinent data that predicts musculoskeletal injuries and derives effective treatment solutions. The biomechanical exam can include a predetermined set of movements to be measured by an enhanced goniometer. Each measurement may include details as to what axis or axes data should be captured with respect to. For example, data associated with a measurement can indicate that measurements should be taken with respect to the z axis of the goniometer and not the x or y axes. Each measurement may also be processed by a computing device corresponding to an enhanced goniometer to determine, based on a given movement to be measured, what axes should be selected in order to generate a measurement result.

According to one general implementation, an enhanced goniometer includes a user interface that guides a physician through a multi-point biomechanical exam. The user interface includes information, e.g., an image, that provides information to the physician on how to perform each step in the biomedical exam. For instance, for a particular biomedical exam, the user interface may illustrate how the physician is to place the goniometer on a patient or hold or move the goniometer, to register an accurate measurement.

The enhanced goniometer may be implemented in any appropriate device that can measure angles in one, two, or three dimensions. To improve accuracy, measurements along certain axes may be disabled, e.g., by temporarily disabling certain hardware or selectively filtering obtained measurement data from a measurement device, when making measurements that do not require those axes to be measured. An indication of active and disabled axes may be illustrated within the user interface.

It is appreciated that methods in accordance with the present disclosure can include any combination of the aspects and features described herein. That is, methods in accordance with the present disclosure are not limited to the combinations of aspects and features specifically described herein, but also may include any combination of the aspects and features provided.

One innovative aspect of the subject matter described in this specification is embodied in a method that includes obtaining a sequence of measurements to be measured based on one or more data points of an examination; receiving input from a user initiating a measurement; receiving raw data from a measuring component; processing the raw data to exclude measurements corresponding to one or more axes; generating a measurement result based on the processed raw data; and providing the measurement result for output.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The foregoing and other embodiments can each optionally include one or more of the following features, alone or in combination. For instance, in some implementations processing the raw data to exclude measurements corresponding to the one or more axes may include: determining a current measurement of the sequence of measurements to be measured based on a predetermined order of the sequence of measurements to be measured; determining elements of data to be excluded based on the current measurement; and processing the raw data from the measuring component by excluding the determined elements of data.

In some implementations, processing the raw data to exclude measurements corresponding to the one or more axes may include: parsing each measurement of the sequence of measurements; and based on parsing each measurement of the sequence of measurements, determining the measurements corresponding to the one or more axes to exclude from the raw data.

In some implementations, the actions may include outputting an image to a display that provides information to the user on how to perform the measurement.

In some implementations, the image may include graphical information indicating where on a body of a patient to position a goniometer device before initiating the measurement.

In some implementations, the sequence of measurements may include a big toe extension measurement.

In some implementations, the sequence of measurements may include a big toe extension measurement followed by a weighted dorsiflexion measurement.

The details of one or more implementations of the present disclosure are set forth in the accompanying drawings and the description below. Other features and advantages of the present disclosure will be apparent from the description and drawings, and from the claims.

BRIEF DESCRIPTION OF THE DRAWINGS

FIG. 6 is a diagram of computer system components that can be used to implement a system for an enhanced goniometer.

Like reference numbers and designations in the various drawings indicate like elements.

DETAILED DESCRIPTION

Figure 1:
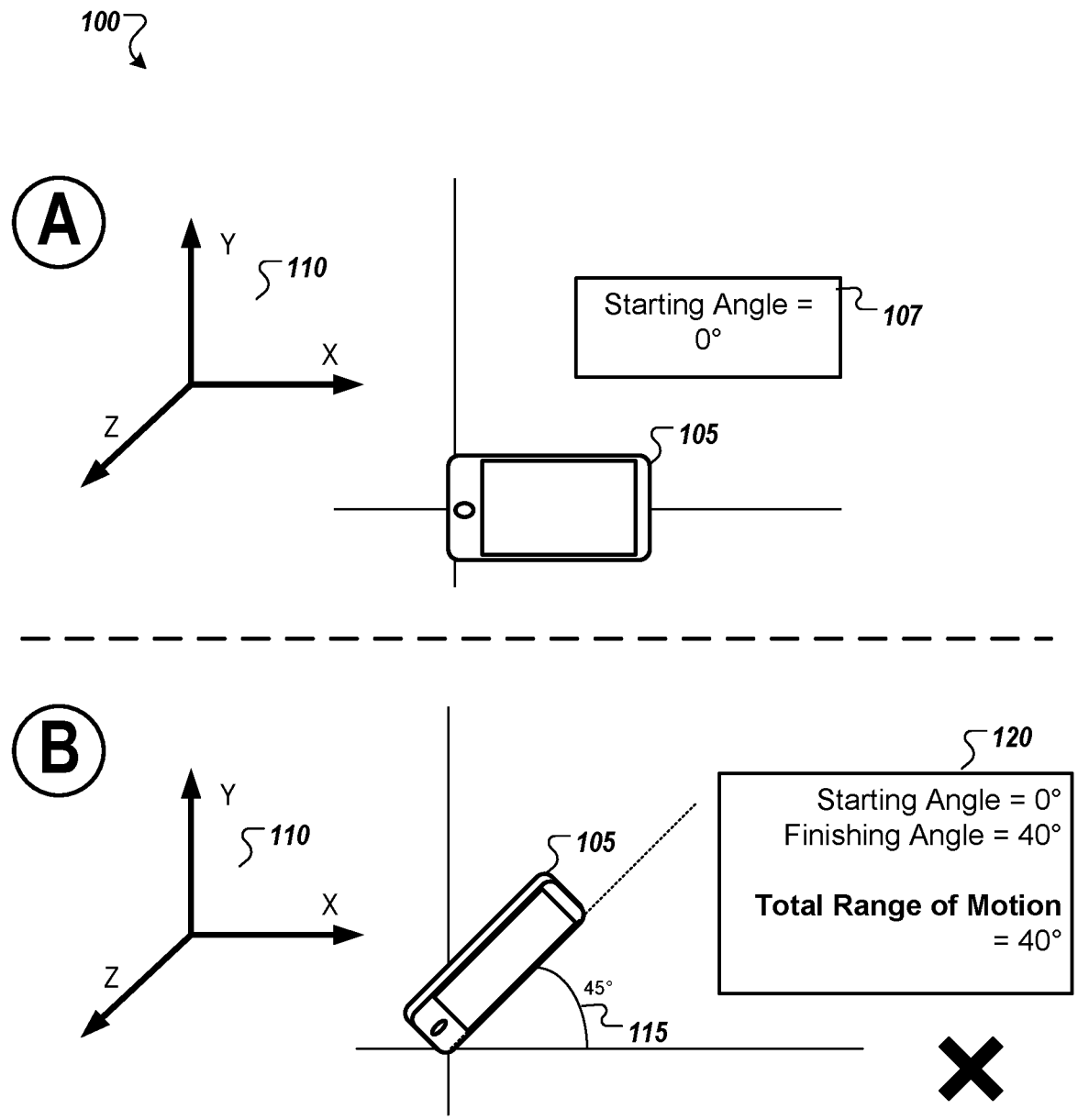
FIG. 1 is a diagram showing an example of a legacy goniometer system.

FIG. 1 is a diagram showing an example of a legacy goniometer system 100. The system 100 includes a device 105 that is measuring an angle in a dimensional space 110. The device 105 can measure angles in one, two, or three dimensions. In the particular example of FIG. 1, the device 105 is measuring an angle in the x y plane about the z axis.

Stage A shows the starting position of the device 105 during a given measurement and stage B shows the finishing position of the device 105. From stage A to stage B, the device 105 rotates about the z axis but also turns relative to a midline of the device 105. Such turning, during the measurement process may impact readings of the device 105. As shown in the example of FIG. 1, the device 105 rotates an angle 115 of 45 degrees about the z axis but, due to the rotation about the midline of the device 105, an angle of 40 degrees is calculated. A suitable user display of the device 105 can display information corresponding to item 107 and item 120 indicating the starting angle and finishing angle of the current measurement.

In the example of FIG. 1, the device 105 is incapable of fully accounting for turning of the device 105 during the measurement. As a result, the wrong angle is indicated to the user. When used in the medical profession, even small inaccuracies may significantly impact diagnosis as well as treatment. Given the likelihood that a user is unable to keep the device 105 in an exact plane over the course of a given measurement, measurement results generated using the device 105 as a goniometer are likely to include inaccuracies.

Figure 2:
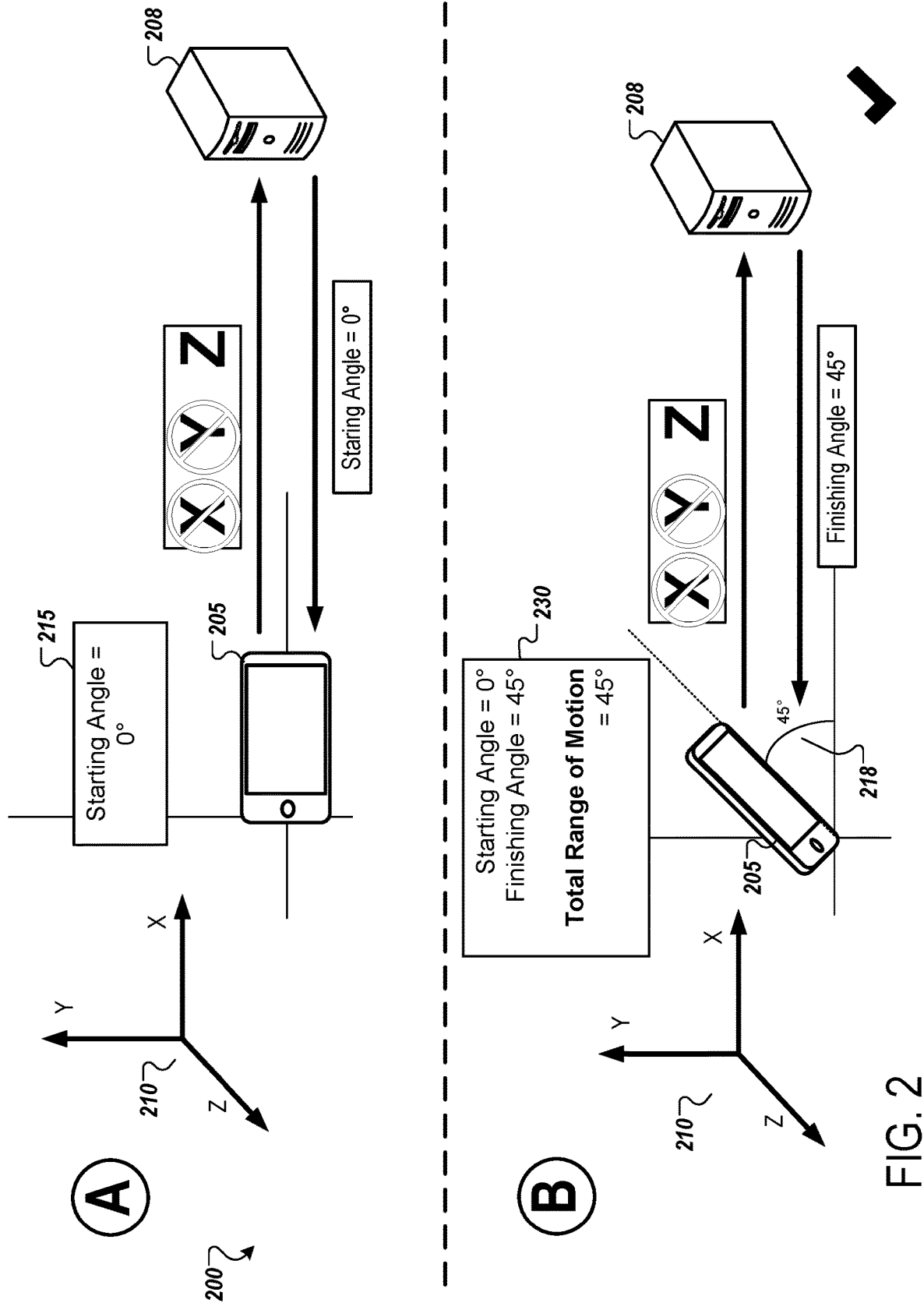
FIG. 2 is a diagram showing an example of an enhanced goniometer system.

FIG. 2 is a diagram showing an example of an enhanced goniometer system 200. The system 200 includes a device 205. The device 205 can measure angles in one, two, or three dimensions. The device 205 is communicably connected to the computing element 208. In some implementations, the computing element 208 is housed within the device 205. For example, the device 205 can be a type of smartphone designed with angle measuring capabilities (e.g., accelerometers) as well as processing capabilities.

Similar to the example of FIG. 1, the device 205 measures an angle about the z axis. In stage A, the device 205 starts parallel with the x y plane at an angle of 0 degrees as shown in item 215. The device is measuring an angle 218 that is 45 degrees with respect to the z axis and rotates about the z axis corresponding to the angle 218. Similar to the device 105 of FIG. 1, the device 205 turns during the course of the measurement, potentially due to unintentional rotation caused by a user, and is no longer parallel with the x y plane in stage B.

Unlike the system 100, the system 200 is able to successfully compensate for the effects of the turning by selecting a subset of measurements in which to process. For example, only measurements corresponding to the angle measurement about the z axis are processed by the computing element 208 and the system 200 is able to correctly determine the angle measured by the device 205 to be 45 degrees as shown in item 230.

In some implementations, the system 200 may warn a user based on a position of the device 205. For example, the system 200 may detect that the device 205 is at a tilt greater than a predetermined number of degrees with respect to a predetermined axis, such as the z axis in dimensional space 210. The system 200 may detect the tilt during measurement of an angle within a measurement sequence. In response to determining that the device 205 is tilted more than a predetermined amount, the system 200 may display a prompt for a user of the system 200 that the device 205 is tilted beyond a threshold and the system 200 may not accept the angle with the device 205 in such an orientation.

Figure 3:
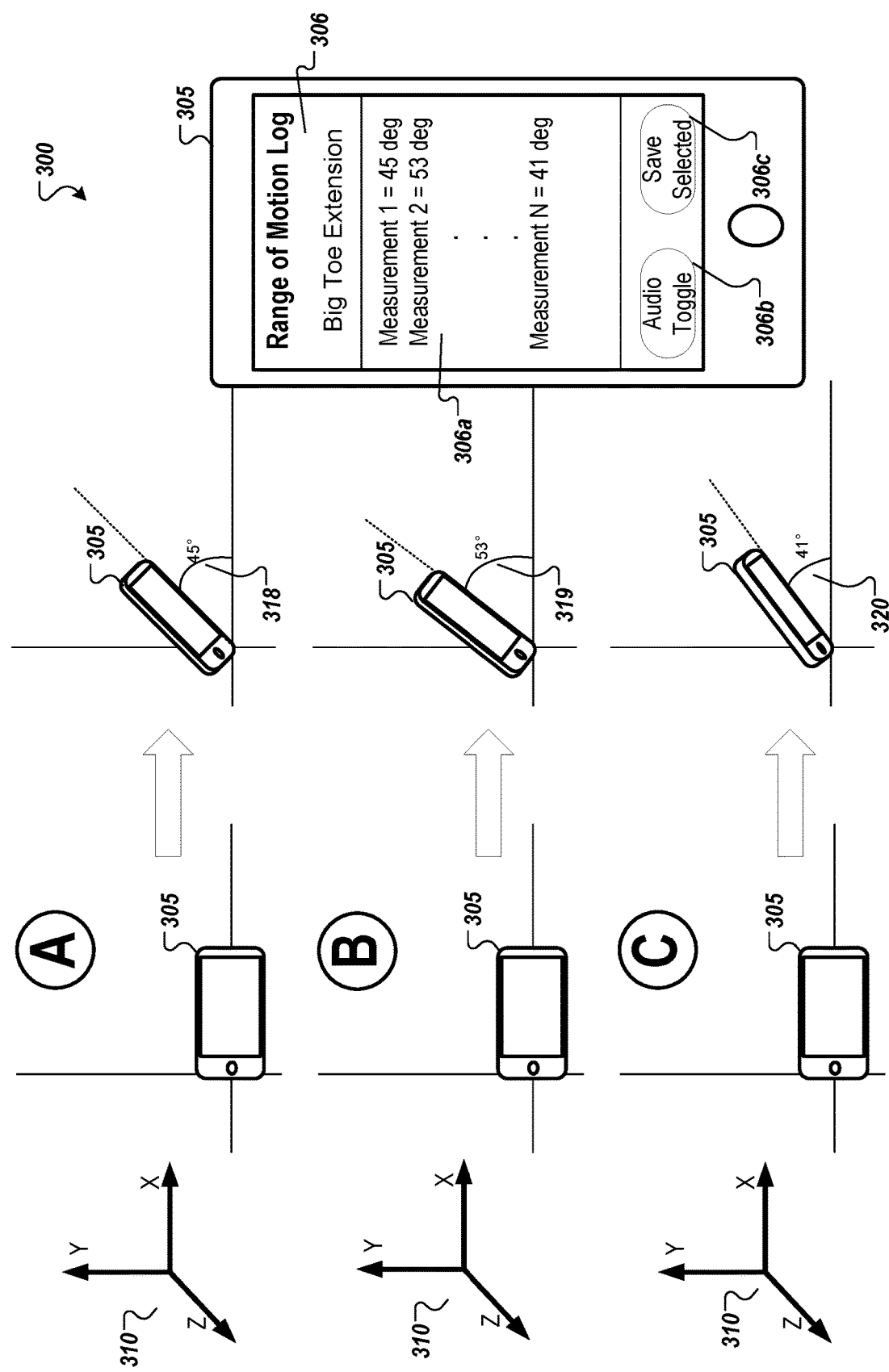
FIG. 3 is a diagram showing an example of taking multiple measurements using an enhanced goniometer system.

FIG. 3 is a diagram showing an example of a system 300 for taking multiple measurements using an enhanced goniometer. The system 300 includes a device 305 that, similar to the device 205, can measure angles in one, two, or three dimensions.

The device 305 performs 3 measurements shown in stages A, B, and C. The device 305 measures a first angle 318 that is 45 degrees, a second angle 319 that is 53 degrees, and a third angle that is 41 degrees. Each of the measurements corresponds to a single point in a multi-point biomechanical examination. Each of the measurements corresponds to a big toe extension where the big toe of a patient is extended upwards relative to the x z plane shown in dimensional space 310 to produce an angle. The device 305 can be used to measure a maximum angle created by the big toe and the floor corresponding to the x z plane.

Although big toe extension is considered in the example shown in FIG. 3, any other angular measurement of a multi-point biomechanical examination can be measured using multiple measurements stored on the device 305. For example, measurements may includes weighted dorsiflexion, tibial rotation, femoral rotation, hip flexion, shoulder flexion, shoulder abduction, cervical rotation, cervical lateral flexion, wrist extension, wrist supination, wrist pronation, among others.

The device 305 can display the multiple measurements, which may be any number of measurements, on a suitable display 306 of the device 305. The multiple measurements can be selectable items which are saved by selecting a save selected button 306c. Each measurement may be read aloud to a user of the device 305 in order to determine the angle without removing the device from a measurement position. Audio of the measurements can be toggled on or off using an audio toggle button 306b. For example, in some cases, the audio of the measurements may be toggled on or off in a settings page of a corresponding application interface.

In some implementations, each successive measurement is captured by the device 305 as a user rotates the device 305 after or during activation of a user input element. For example, the device 305 may be equipped with buttons along one edge of the device 305. In order to start a new measurement, the user may press one or more buttons along the edge of the device 305.

In one example, the user may then release the one or more buttons, rotate the device 305 according to a current measurement requirement, and again press the one or more buttons to stop the measurement. The button to start the measurement may be the same as, or different than, the button used to stop the measurement.

In another example, the user may press one or more buttons along the edge of the device 305 and continue to press the one or more buttons for the entirety of the measurement. After the measurement is complete, the user may release the one or more buttons to end the measurement. A processing component corresponding to the device 305 may then determine a value for the given measurement according to one or more methods of this disclosure.

In some implementations, the rotational discrepancies during a measurement process, such as the rotation of the device 305 about the midline of the device 305 in stages A, B, and C are caused, at least in part, by the pressing of one or more buttons along the edge of the device 305 used for starting or stopping a measurement process. For example, a user may readjust a grip of the phone in order to press the one or more buttons which may cause rotation about an axis other than the current measurement axis, such as the z axis in FIG. 3.

In order to ensure that rotational discrepancies for any movement not directly related to the measurement of a biomechanical movement of the patient, such as rotation about the midline of the device 305, do not result in angle measurement inaccuracies, a computing component corresponding to the device 305 can be used to exclude angle measurements corresponding to one or more axes. In the example of FIG. 3, an angle is to be measured about the z axis. Once determining that angle measurements are to be measured about the z axis based on a given measurement (e.g., big toe extension, among others), a computing component communicable connected to the device 305 can exclude measurements corresponding to the x and y axes.

The value of any given measurement can be shown on a display of the device 305. For example, portion 306a of the display 306 shows all measurements corresponding to the current data point.

Figure 4:
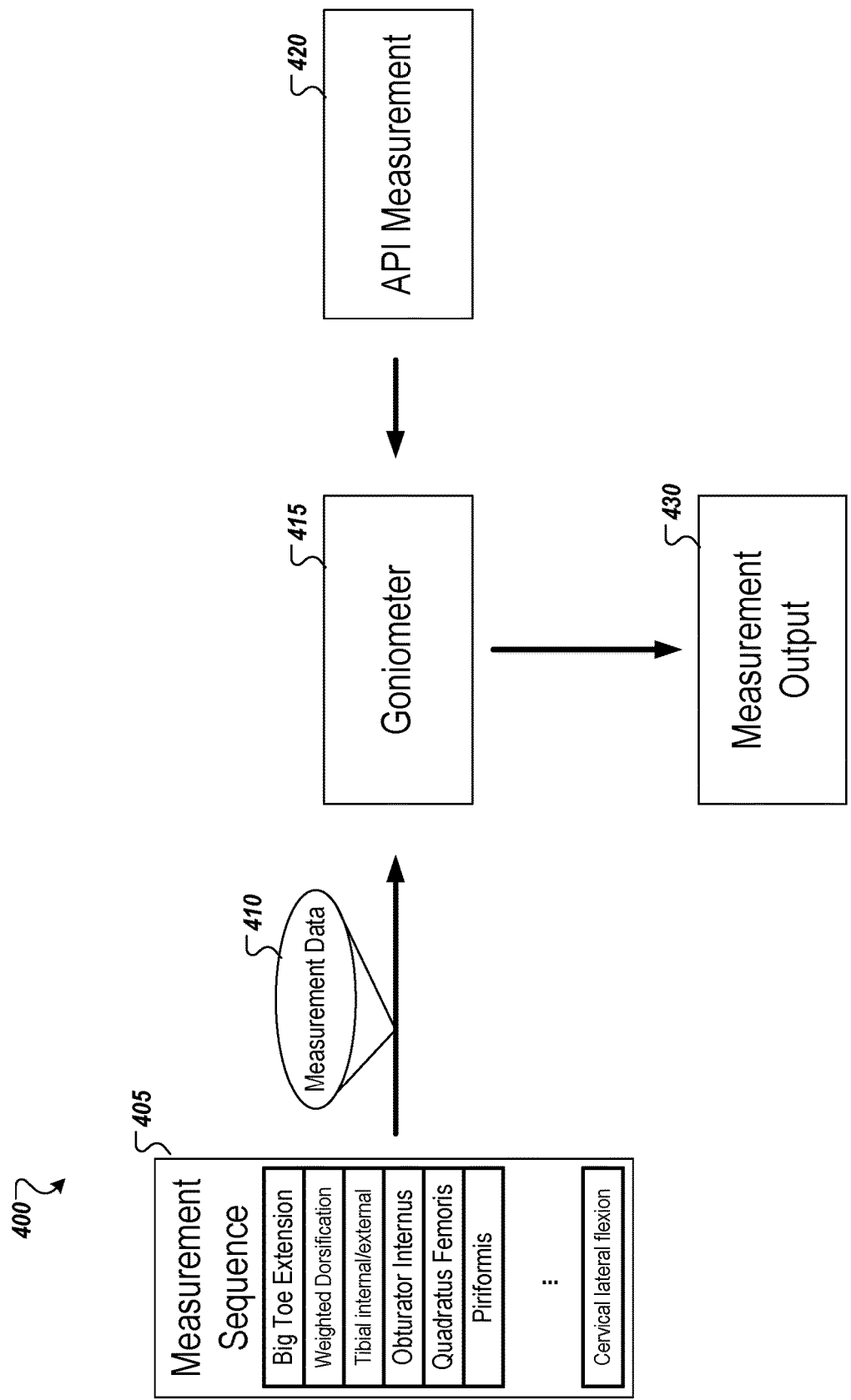
FIG. 4 is a diagram showing an example process flow for an enhanced goniometer system.

FIG. 4 is a diagram showing an example process flow 400 for an enhanced goniometer. A goniometer 415 receives measurement data 410 corresponding to a measurement sequence 405. The goniometer 415 also receives data from an application programing interface (API) 420. In some cases, the API 420 operates using components of a device corresponding to the goniometer 415. The goniometer 415 generates, based on the data 410 and the API 420, a measurement output 430 corresponding to a particular measurement within the measurement sequence 405.

The measurement sequence 405 may align with a multi-point biomechanical examination where each measurement of the measurement sequence 405 is used to compute at least one data point in the examination. The measurement sequence 405 shows a number of example measurements including: big toe extension, weighted dorsification, tibial internal/external, obturator internus, quadratus femoris, *piriformis*, and cervical lateral flexion.

The measurement sequence 415 can be either stored locally on a component communicably connected to the goniometer 415 or remotely on another component and sent to the goniometer 415 over one or more networks for data transfer.

In some implementations, the measurement sequence 405 is maintained on a server. For example, a server can store the measurement sequence 405 and be communicably connected to the goniometer 415 such that, when changes are made to the version maintained on the server, the changes are obtained by the goniometer 415 and incorporated into a current set of measurements. In this way, updates to a measurement sequence can be pushed from a central location out to goniometers in the field when updates to a sequence are required.

The goniometer 415 may include a device used to obtain raw measurement data such as the device 205 or 305. The device may be a type of smartphone that includes a display and internal processing components. The device may also be able to perform operations of the API 420 such as accelerometer measurements among others in order to obtain raw data from multiple axes related to angle measurements.

The goniometer 415 can use the measurement data 410 to determine how to process the raw data from the API 420. For example, the goniometer 415 can determine one or more axes for data collection and disable another set of axes in order to isolate a particular set of axes for measurement. The goniometer 415 may determine what axis, or axes, to disable based on the measurement sequence 405. In particular, the measurement data 410 may be configured by the goniometer 415, or a third party system, to include one or more indications of one or more measurements of the measurement sequence 405. The one or more indications can include alphanumeric characters configured for each measurement of the measurement sequence 405. Each measurement of the measurement data 410 can be parsed by the goniometer 415. After parsing, the goniometer 415 can determine, based on a determined measurement and a determined axis of measurement for the measurement, what axis, or axes, to disable for the given measurement. By isolating the selected measurements based on the measurement data 410, the goniometer 415 can successfully compensate for unintentional torsion of any component of the goniometer 415.

In some implementations, the goniometer 415 may track measurements to determine what measurement in the measurement sequence 415 is currently being measured. For example, the measurement data 410 can include, at least, an indication of a big toe extension measurement followed by a weighted dorsiflexion measurement followed by a tibial internal measurement. The goniometer 415 can determine what axis, or axes, are to be disabled for each measurement included in the measurement data 410 based on the measurement sequence 415.

In some implementations, the goniometer 415 may track each measurement to determine what measurement is being performed. For example, after a result for the big toe extension measurement is generated based on disabling one or more axes, the goniometer 415 determines, based on the known order of the measurement sequence 415 included in the measurement data 410, the next measurement of weighted dorsification and automatically applies a corresponding axis disablement for the weighted dorsiflexion. In some implementations, the goniometer 415 can determine the next measurement and what one or more axes to disable in real time as a user is readjusting to perform the next measurement. In this way, the data extraction for the biomechanical exam is made, not only more accurate, but more efficient as the accuracy improvements enabled, in part, by axis disablement are automatically applied as a user performs each measurement according to the measurement sequence 415.

In some implementations, the measurement data 410 includes what measurements to process. For example, the measurement data 410 corresponding to big toe extension may include data indicating that measurements of the big toe extension should only involve processing of the angle measurements relative to the z axis and angle measurements relative to the x and y axes are to be disabled. Based on the measurement data 410, the goniometer 415 can process the raw data from the API 420 based on angle measurements relative to the z axis.

In some implementations, the goniometer 415 determines, based on the measurement data 410, what measurements to disable from the API 420. For example, without receiving explicit data indicating what measurements to disable, the goniometer 415 can parse the measurement sequence 405 corresponding to the measurement data 410 and determine, based on a name or other data corresponding to a given measurement, what measurements from the API 420 should be disabled.

In some implementations, data from a component of the goniometer 415 is used to determine what measurements to disable. For example, a device of the goniometer 415 can use an onboard accelerometer to determine a starting position of the device. The device can be a smartphone or other similar device. The starting position can be used, at least in part, to determine what measurements to disable from the API 420. For example, if the device starts parallel to the x y plane, the goniometer 415 can disable measurements corresponding to the x or y axes based on determining that the measurement will likely be an angle measurement about the z axis.

In some implementations, the name of a measurement can indicate that a particular angle is one dimensional as opposed to multi-dimensional. For example, extension may indicate, when parsed, that a corresponding measurement is a one dimensional measurement.

In some implementations, the goniometer 415 receives data from the API 420 that is not consistent with possible results for a given measurement. For example, for a big toe extension, if the data from the API 420 corresponds to an angle greater than 180 degrees, indicating that the big toe was able to extend 180 degrees from resting position, the goniometer 415 can determine that the data from the API 420 is incorrect. In some implementations, after determining the data from the API 420 is incorrect based on the given measurement indicated in the measurement data 410, the goniometer can output to a display that the measurement was invalid and request a user to retake the measurement.

In some implementations, one or more acceptable ranges are referenced by the goniometer 415. For example, in order to determine if data for a given measurement is possible and not an error in the measurement system, the goniometer 415 can obtain data from the API 420 and generate an angle measurement based on the processes described herein. After generating the angle measurement, the goniometer 415 can compare the generated angle measurement to one or more values indicating acceptable ranges for measurements included in the measurement sequence 405. In some cases, the acceptable ranges are indicated in the measurement data 410 and sent to the goniometer 415.

Figure 5:
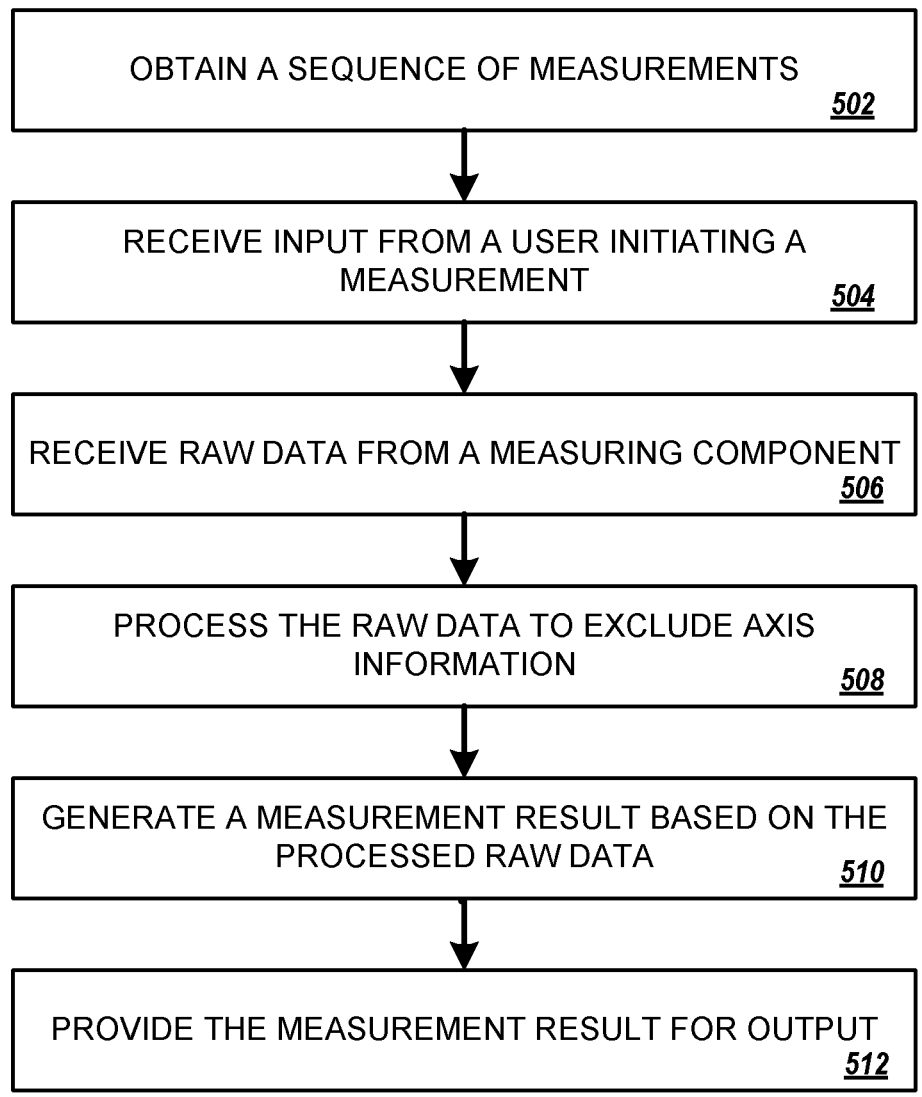
FIG. 5 is a flow diagram illustrating an example of a process for an enhanced goniometer system.

FIG. 5 is a flow diagram illustrating an example of a process 500 for an enhanced goniometer. The steps of the process 500 may be performed by one or more electronic systems, for example, the system 200 or the system 300.

The process 500 includes obtaining a sequence of measurements (502). For example, as shown in the process flow 400, the goniometer 415 obtains the measurement data 410 corresponding to the measurement sequence 405. In some cases, the measurement data 410 comprises data that indicates one or more measurements included in the measurement sequence 405.

The process 500 includes receiving input from a user initiating a measurement (504). For example, as shown in FIG. 2, the user may handle the device 205 and rotate the device 205 by an angle that matches a movement of a patient. For example, the user can move the device 205 from a baseline, such as a line parallel to a floor represented by the x z plane in dimensional space 210, to the angle of an extended big toe for the measurement of a big toe extension.

The process 500 includes receiving raw data from a measuring component (506). For example, as shown in the process flow 400, the goniometer 415 receives data from the API 420. In some case, the API 420 generates raw data based on, at least, one or more accelerometers. The accelerometers may be housed within a device of the goniometer 415 used to measure an angle of a biomechanical movement. By measuring changes in acceleration, the accelerometers can determine an angle of rotation corresponding to one or more axes of rotation.

In some implementations, the accelerometers of a device of a goniometer are housed in the device so as to be affected by the unintentional rotation of the device. For example, if the device used for the enhanced goniometer houses an accelerometer in the center of the body of the device, rotation about the edges of the device may cause the accelerometers to be in a position different from the position desired for an accurate measurement. Without further processing by the goniometer 415 as described in this specification, these unintentional rotations can cause inaccuracies in the resulting angle measurements used in one or more data points of a biomechanical exam.

In some implementations, the unintentional rotation of a device may be captured and used to determine the actual location of the accelerometer with respect to a given axis of rotation. For example, in the case of rotation about the z axis, unintentional rotation may occur that rotates the device about a long edge of the device. This rotation may affect the location of the accelerometer chip inside the device and may therefore affect a reading of an angular measurement measured about an axis, such as the z axis.

In order to determine the actual location of the accelerometer, the rotations of the device may be recorded by a component such as the API 420 and processed by the goniometer 415 to calculate the differential motion of the accelerometer chip with respect to the angle to be measured. In this way, the goniometer 415 can determine an accurate angle measurement even if unintentional rotation causes the accelerometer to be rotated out of the plane of measurement, e.g., the x y plane about the z axis in FIG. 2.

In some implementations, a user is asked to measure an angle with a device using one edge of the device to ensure accuracy. For example, in order to compensate for unintentional rotation, a user may be prompted by a user interface to ensure that at least one edge of the device, such as an edge of the device 305, is made parallel with the reference, such as the x z plane, and an aspect of a human body being examined, such as a big toe extension in the x y plane.

In this way, an enhanced goniometer may compensate for unintentional movement that may result in an accelerometer chip of the device 305 being higher, lower, left, or right, of an accurate position to measure the angle. Based on the recorded movements, a goniometer, such as the goniometer 415 can calculate what would have been the location of an accelerometer chip of a corresponding device had the user not unintentionally rotated the device, such as the device 305, of the goniometer 415. The goniometer 415 can calculate the unrotated location of the accelerometer chip using the known location of the accelerometer chip in reference to the body shape of a corresponding device for measurement, such as the device 305, and based on at least one edge of the device 305 being parallel with an aspect of the patient being measured, such as the big toe.

The process 500 includes processing the raw data to exclude axis information (508). For example, as shown in FIG. 2, a particular goniometer includes both the device 205 and the computing component 208. The computing component 208 excludes measurements corresponding to the x and y axes of rotation as shown in the dimensional space 210. In this way, the effects of rotation about the midline of the device 205, or any other accidental torsions of the device 205 during the measurement process, are mitigated and the device 205 and the computing component 208 can generate an accurate measurement of the angle 218.

The process 500 includes generating a measurement result based on the processed raw data (510). For example, the goniometer 415 can use the exclusions applied to the API 420 to generate a measurement result. In some cases, the measurement result includes an angle measurement about a single axis such as a z axis. The z axis can be relative to a patient, measurement, or relative to the face of a device.

In some implementations, the goniometer 415 may determine what the current measurement is based on the known order corresponding to the measurement sequence 405 and included in the measurement data 410. Based on the current measurement determined based on the measurement sequence 405, the goniometer 415 can determine what axis, or axes, should be disabled in order to achieve an accurate result for the current measurement. The goniometer 415 can adjust what axes to disable for each measurement of the measurement sequence 405 in order to generate a measurement result for each measurement of the measurement sequence 405. Each measurement may have its own unique set of axes, or other measurement data, to be disabled in order to achieve an accurate measurement result.

The process 500 includes providing the measurement result for output (512). For example, the goniometer 415 can output the measurement result generated based on excluding one or more axes of measurement to a display. For example, as shown in FIG. 3, the device 305 is equipped with the display 306. The portion 306a of the display 306 can be used to show one or more measurement results generated by a computing component communicably connected to the device 305.

FIG. 6 is a diagram of computer system components that can be used to implement a system for an enhanced goniometer. The computing system includes computing device 600 and a mobile computing device 650 that can be used to implement the techniques described herein. For example, one or more components of the system 200, 300, or 400 could be an example of the computing device 600 or the mobile computing device 650, such as a computer system implementing the device 205, the computing component 208, the device 305, or the goniometer 415, among others.

The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, mobile embedded radio systems, radio diagnostic computing devices, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. In addition, multiple computing devices may be connected, with each device providing portions of the operations (e.g., as a server bank, a group of blade servers, or a multi-processor system). In some implementations, the processor 602 is a single threaded processor. In some implementations, the processor 602 is a multi-threaded processor. In some implementations, the processor 602 is a quantum computer.

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or include a computer-readable medium, such as a floppy disk device, a hard disk device, an optical disk device, or a tape device, a flash memory or other similar solid-state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine readable mediums (for example, the memory 604, the storage device 606, or memory on the processor 602). The high-speed interface 608 manages bandwidth-intensive operations for the computing device 600, while the low-speed interface 612 manages lower bandwidth-intensive operations. Such allocation of functions is an example only. In some implementations, the high speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device, such as a mobile computing device 650. Each of such devices may include one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may include appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (nonvolatile random access memory), as discussed below. In some implementations, instructions are stored in an information carrier such that the instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry in some cases. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), LTE, 5G/6G cellular, among others. Such communication may occur, for example, through the transceiver 668 using a radio frequency. In addition, short-range communication may occur, such as using a Bluetooth, Wi-Fi, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, among others) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

According to one general implementation, the present specification describes an enhanced goniometer including a user interface that guides a physician through a multi-point biomechanical exam. The user interface includes information, e.g., an image that provides information to the physician on how to perform each step in the biomedical exam. For instance, for a particular biomedical exam, the user interface may illustrate how the physician is to place the goniometer on a patient or hold or move the goniometer, to register an accurate measurement.

In some implementations, a device of the goniometer shows the user interface on a display of the device. For example, in FIG. 3, the display 306 of the device 305 can be used to show a user interface that guides a physician or user through a multi-point biomechanical exam. A physician or user can view the user interface on the display 306 and then proceed to perform measurements, based on the tutorial shown on the user interface, of a biomechanical movement. The measurements can include one or more angle measurements as shown in stages A though C in FIG. 3.

The enhanced goniometer may be implemented in any appropriate device that can measure angles in one, two, or three dimensions. To improve accuracy, measurements along certain axes may be disabled, e.g., by temporarily disabling certain hardware, when making measurements that do not require those axes to be measured. An indication of active and disabled axes may be illustrated within the user interface.

The enhanced techniques and devices described by this specification address musculoskeletal injuries that cost companies millions of dollars in worker's compensation claims and health insurance cost every year, and, in the case of a sports organization time, incur significant player time lost with players on the disabled list.

In regard to the labor force, the World Health Organization states that, "the lifetime prevalence of non-specific (common) back pain is estimated at 60% to 70% in industrialized countries."

The American Academy of Orthopaedic Surgeons reports: "In 2004, 25.9 million persons lost an average of 7.2 days of work due to back pain—a total of 186.7 million work days lost that year."

The Bureau of Labor Statistics reports that "overexertion and bodily reaction" accounted for the largest percentages of missed work—particularly among laborers and freight, stock and material movers and nursing assistants. To be specific, they state that, "of the 443,560 sprain, strain and tear cases reported in 2012, 63% were the result of overexertion and bodily reaction." Of that 63%—the highest majority were to the back (36%), with the next highest being the shoulder (13%) and the knee (12%).

In regard to sport organizations, according to 2016 statistics, as of October 7, there were 113 players on the disabled list, accounting for $396 million in salaries, or 12.4 percent of payroll in all of MLB.

2018 Statistics: As of February 12, 3,798 games missed due to injury, up 42 percent from the same portion of games last season in all of NBA.

2019 Statistics: A total of 50.9% of all NHL players missed at least one game within a season of play, and injuries represented a total salary cost of approximately US$218 million per year. Head/neck injuries and leg/foot injuries were the most expensive in terms of overall cost, while head/neck and shoulder injuries had the highest mean cost.

The average team in the NFL loses $11,500,000 on injured athlete's base salaries alone each season and we have shown that after an initial spend of $70,800,000 to win one game, each extra win requires an additional $2,300,000 worth of players available.

Injuries play an immense role in a team's likelihood of success. Given that we know certain injuries are preventable and that there are numerous modifiable risk factors, this gives rise to the importance of appropriate management and the use of analytics not just to showcase the problem, but to solve it.

The enhanced techniques and devices described by this specification create a risk-mitigation/operational cost reduction strategy and injury prevention model based on a biomechanical exam, along with medical biomarkers, qualitative and quantitative questioning. An exam may yield data used in a treatment/exercised-based model to either prevent or treat the injury assessed and reduce worker's compensation claims, health insurance cost, and in regards to sport organizations time lost due to injury which cost teams millions of dollars.

Alternatives, such as corporate wellness programs that incorporate nutritional initiatives, in-house gyms and exercise classes, wearable devices aimed at tracking data such as sleep patterns, steps, among others, are implemented with hopes of increasing the overall health of the employees and preventing such things such as heart attacks, strokes and diabetes.

Disadvantages of these alternatives may include the fact that the data collected is not necessarily used to create a specific and individualized health approach for that employee or athlete. While these alternatives may, if the employee/athlete is held accountable and is self-motivated, raise his or her overall health and/or decrease their chances of injury, it will not predict, help avoid or treat specific non-traumatic musculoskeletal injuries. Non-traumatic injuries make up the majority of the company's worker's compensation claims and in the world of sports time spent on the disabled list as opposed to trauma induced or acute illnesses such as heart attacks, strokes, among others.

The aspects described in this specification, including the enhanced goniometer and methods of using the enhanced goniometer, can be used to predict and address non-trauma induced musculoskeletal injuries. As mentioned above, non-traumatic musculoskeletal injuries such as low back pain, hip pain, repetitive stress injuries make up the majority of worker's compensation claims and time lost on the disabled list. The effects of such musculoskeletal injuries represent a large expense to companies and/or organizations.

A biomechanical screening, based at least in part on a biomechanical exam, collects data directly related to the biomechanics of the musculoskeletal structures responsible for the movement behind the daily regular tasks employees and athletes need to perform. Any aberrances in this data point to an injury that has already happened or predicts one in the future. The treatment approach is directly related to the data collected from this screening and is monitored to insure data returns to normal ranges.

According to one example implementation, the enhanced techniques described by this specification include a detailed, sixteen-point biomechanical exam. This group of sixteen data points can include one or more of the following ranges of motion: Big Toes Extension, Weighted Dorsiflexion, Tibial internal/external rotation, Obturator Internus, Quadratus Femoris, *Piriformis*, Thoracic/Lumbar junction, Shoulder Flexion, Shoulder External Rotation, Shoulder External Rotation with Flexion, Wrist Pronation, Wrist supination, Wrist Flexion, Wrist Extension, Cervical rotation/extension, and Cervical lateral flexion.

One or more of the ranges of motion in the sixteen-point biomechanical exam can be measured by an enhanced goniometer using the methods described herein. For example, the enhanced goniometer can be used to measure the angle of a toe in order to obtain data related to the Big Toes Extension data point of the sixteen-point biomechanical exam.

This grouping of data points was discovered over years of treating thousands of athletes and clients. This specific set of data points has demonstrated to be very predictive in nature for multiple musculoskeletal injuries.

Each data point collected via a hardware tool, such as one or more components of an enhanced goniometer, is then organized using a software tool, and then processed through an algorithm which will highlight a specific color (e.g., red, yellow or green).

The color attributed to each data point is based on a Key Performance Indicator (KPI). The KPI for each data point is based on years of empirically collected data that is now being calculated via an algorithm by the software platform.

In some implementations, the software platform can be a component of the enhanced goniometer. For example, if a smartphone is used as a component of the enhanced goniometer, the smartphone can be used to process data as the software platform to assign a KPI for a given data point based on obtained data.

In some implementations, the software platform can be a server communicably connected to the enhanced goniometer. For example, the enhanced goniometer can obtain raw data for a data point of a biomechanical exam. The enhanced goniometer can then send the data to a server functioning, in part, as a software platform such that the server assigns a KPI based on the data obtained by the enhanced goniometer for a given data point.

In the software platform, and according to this example, green highlighting indicates a data point that is within a range of what is considered normal, and indicates optimum joint mechanics, establishing that the athlete is least susceptible to a non-traumatic injury. Yellow highlighting indicates a data point that is within a range outside of what is considered normal, but with less than optimal joint mechanics, indicating a greater probability to a non-traumatic injury. Red indicates a data point that is within a range outside of what is considered normal, indicating a higher probability of non-traumatic injury.

The KPIs not only determine when to take action in terms of treatment but also the type of treatment and exercises that are needed to change data for the better. Data is then monitored by the platform throughout the treatment/intervention and modified according to how data points/colors change during re-examinations.

In regard to the Kinetic Chain, anatomically speaking, the kinetic chain refers to the interrelated groups of body segments, connecting joints, and muscles working together to perform movements and the portion of the spine to which they connect. These movements consist of everyday task we do all the way to the more intricate movements in the world of professional sports.

The upper kinetic chain includes of the fingers, wrists, forearms, elbows, upper arms, shoulders, shoulder blades, and spinal column. The lower kinetic chain includes the toes, feet, ankles, lower legs, knees, upper legs, hips, pelvis, and spine. In both chains, each joint is independently capable of a variety of movements. Dependent on whether the distal end of the chain is fixed or free to move without restriction, each movement is classified as either closed or open.

To complete movement efficiently, each joint and muscle working together not only needs to move symmetrically, but specific ranges of motion are needed to maintain the most efficient and long term movement patterns of each segment. From the toes to the upper torso, any lack of proper mobility, strength, and/or stability may cause improper movement patterns. The term 'compensation' comes to mind. Over time compensatory patterns, which include improper range of motion, strength, and stability begin to stress the body. This stress leads to chronic pain, discomfort, and or even musculoskeletal injury.

Synovial joints allow the body a tremendous range of movements. Each movement at a synovial joint results from the contraction or relaxation of the muscles that are attached to the bones on either side of the articulation. The type of movement that can be produced at a synovial joint is determined by its structural type. While the ball-and-socket joint gives the greatest range of movement at an individual joint, in other regions of the body, several joints may work together to produce a particular movement. Overall, each type of synovial joint is necessary to provide the body with its great flexibility and mobility. There are many types of movement that can occur at synovial joints. Movement types are generally paired, with one being the opposite of the other.

In regard to physiology and neurology, patterns of compensation develop in human movement for a multitude of reasons. From injuries to "daily life activities," the human body is constantly being shaped and re-modeled through mechanotransduction, which is the process in which biomechanical forces in combination with biochemical reactions and energy flows literally 'deform' (or change the form of) each and every cell.

In addition, mechanotransduction manipulates and modifies corresponding strands of DNA. In other words, human movement continuously shapes and re-shapes the human body. A pattern of compensation is the body's attempt to make up for the lack of movement in one area by adding a new movement. More specifically, a compensation pattern is a neuromuscular strategy of including a 'new' firing sequence (e.g., motor units and muscles) and/or utilizing structural reliance (e.g., bones, ligaments, tendons, fascia and joint structures) to supplement or avoid another firing sequence and/or structural reliance.

In order to perform any movement accurately—whether that means reaching for a glass of water without knocking it over, or skating across an ice rink without falling—the brain has to learn exactly which muscles to activate, and in what manner.

In regard to core concepts of movement, including reciprocal inhibition, cross correlation, medial vestibular pathway, reciprocal inhibition is a neuromuscular reflex. An increase in neural drive of a muscle, or group of muscles, reduces the neural activity of functional antagonists. This plays a significant role in improving the efficiency of the human movement system, and creating ideal arthrokinematics, e.g., movement of joint forces. This more nuanced definition encompasses the role of reciprocal inhibition in more complex issues in human movement science. Likely the most important point made in this definition is the terms "increase" and "reduction" implying that reciprocal inhibition is not a simple function of "on or off".

For example, postural dysfunction resulting in adaptive shortening and hypertonicity inhibits functional antagonist (tight psoas-inhibited glutes), but does not decrease the neural drive to the glute complex completely making it possible to move and function (although less than optimally).

In regard to cross connection, the nervous system communication that is in play for you to create asymmetrical movements simultaneously is left-right brain integration; both hemispheres of the brain working as a partnership.

For example, the contralateral movement is a limb from one side of the body doing something different to those on the other side, but it can also include any movement that crosses over the midline, right hand touching left knee for instance, left-right brain communication matters for full cognitive function. Developmental diseases and abnormal information processing (such as autism and schizophrenia) have been linked to a "dysfunctional integration among neural systems", suggesting that optimal balance between the hemispheres is vital.

In regard to neuroplasticity, our brains are constantly being reshaped through experience. With every repetition of thought, emotion, and movement we enforce a new neural pathway aiding to a stronger cortical pathway in the brain. Neuroplasticty refers to the muscle building of the brain and through repetition, proper movement control, and symmetry; muscular imbalances can be fixed and/or changed to decrease the chances of musculoskeletal injuries.

In regard to vestibular medial pathway, the medial vestibulo-spinal tract is the path by which input from the vestibular sensory apparatus is used to coordinate orientation of the head and body in space. The vestibular system senses angular and linear acceleration of the head in three dimensions and is responsible for generating vestibulo-ocular and vestibulo-spinal reflexes that stabilize the visual image on the retina and adjust posture (respectively), during head movement.

However, this sensory system also has a role in cognition. Our interaction with our environment comes through our five senses. We are constantly trying to interpret the world we are in, whether we are completing everyday task all the way to the top level of sports. Brain and behavior is a term used to describe the interaction that we as humans have to the world around us. The mechanism behind taking in information root from our body awareness in space and time. Motor skills and/or motor learning is the body's ability to complete/learn a task given the information at hand.

Vestibular Spinal Pathway has a profound influence on the activation of the pelvic floor muscles. When you activate the vestibular system through head movements and eye movements, they activate the ipsilateral pelvic floor muscle. For example, when you do head rotation to the left, it activates the left cerebellum and left vestibular spinal pathway and left pelvic floor muscles An analysis corresponding to the vestibular system may include:
   a. Rotation and (R-VOR)-Rotational Vestibular Ocular Reflex
      i. Horizontal Rotation (Left or Right)
      ii. Vertical Rotation (Flexion or Extension)
   b. Translational (T-VOR)—Translational Vestibular Ocular Reflex
      i. Saccule
         1. Up and down
         2. Forward and Back
      ii. Utricle
         1. Straight Line Horizontal left or right
         2. Head Tilting
   c. Notes
      i. Horizontal Rotation can also stimulate the Utricle
      ii. Flexion and Extension can stimulate the Saccule
Utricle—Is the linear vestibular area
   a. Utricle on the left gets activated with left head tilt
   b. Left head rotation
   c. Left linear horizontal movement like a skater to the left with eyes fixating on a target
   d. Utricle on the left has profound influence on the Vestibular Spinal Pathway
   e. Left Vestibular Spinal Pathway has profound influence on the left pelvic floor muscles An analysis may include a 'Look at Head' procedure as follows:
   a. If they have a left head tilt and the left eye is lower than the right than the left utricle is weak
   b. To correct the left head tilt vertical head movements or vertical tracking exercises
      i. They both correct the T-VOR (Translational VOR)
   c. Then progress the client to Horizontal Head movements or tracking eye movements to the right An analysis may include a 'Look at Romberg' procedure as follows:
   a. If they Sway left, and have left head tilt with the left eye lower than they have a weak Utricle on the left and a weak left Vestibular Spinal pathway on the left and weak left pelvic floor muscles and compensation in the spine like the multifidi
   b. They will also have decreased hip internal rotation range of motion The Left Cerebellum and the left Vestibular Spinal Pathway may be improved with one or more of the following:
   a. Head movements
   b. Eye movements
   c. Skater with visual fixation then will
   d. The following will improve
      i. Left pelvic floor muscle activation
      ii. Left pelvic stability
      iii. Left improve hip internal range of motion According to another general implementation, the enhanced techniques described by this specification may include a nineteen-point biomechanical examination, and/or the enhanced devices described by this specification may aid a physician in performing this examination. In some implementations, the enhanced techniques described by this specification may include a twenty-one-point biomechanical examination that includes femoral internal rotation and shoulder extension. In general, the number of points used in an assessment may depend on the sport or physical role that a person may perform.

For example, the enhanced goniometer may be used to measure angles related to one or more data points of a given biomechanical examination including the nineteen-point biomechanical examination. In general, any number of points can be used to generate a biomechanical examination based on requirements of the given examination.

The nineteen-point biomechanical examination may include:

Data point 1—Big toe extension

Big toe extension, affects the lateral sling of the lower leg and the firing of the gluteus medius. Differential diagnosis: Plantar fasciitis, IT band syndrome, low back pain, lateral meniscus.

Data point 2—Weighted Dorsiflexion

Differential diagnosis: ankle injury, shinsplints, potential Achilles injury, posterior knee pain.

Data points 3 & 4—Tibial rotation. Internal and External

Tibial rotation, can show you the hip ankle relationship, potential meniscus problems, pes anserine, and, most importantly, knee integrity.

Data point 5—Femoral external rotation

In some implementations, femoral external rotation may be performed with extension. For example, the patient may flex their contralateral hip which can put the opposite hip in extension and externally rotate the opposite leg. The measurement may include measuring, from a given starting position, the opposite leg or the flexed leg depending on implementation.

In some implementations, the examination may include femoral internal rotation. The femoral internal rotation may be performed with extension. For example, the patient may flex their contralateral hip which can put the opposite hip in extension and internally rotate of the opposite leg. The measurement may include measuring, from a given starting position, the opposite leg or the flexed leg depending on implementation.

Data point 6—*Piriformis*

Differential diagnosis: Sciatica, low back pain, herniated disc, hip disfunction (labrum tear, arthritis, cam lesion), and sports hernia.

Data point 7—Quadratus femoris

Differential diagnosis: Upper hamstring injury, gluteus medius firing.

Data 8—Obturator internus

Differential diagnosis: Integrity of the hip joint, cam lesions, integrity of the lumbar facet, Low back pain, herniated disc, sports hernia.

Data point 9—Hip extension

Differential diagnosis: Camel lesion, herniated disc, facet syndrome, abdominal tear/sports hernia, low back pain, hip flexor bursitis, torn rectus femoris.

Data point 10—Hip flexion

Data point 11—Thoracic Lumbar junction

Differential diagnosis: Oblique strain, low back pain, thoracic pain, ipsilateral shoulder.

Data point 12—Shoulder flexion

Differential diagnosis: Shoulder impingement syndrome, scapular dysfunction, ipsilateral latissimus dorsi, tightness, shoulder bursitis.

Data point 13—Shoulder abduction external rotation 30 degrees

Differential diagnosis: impingement syndrome, capsulitis, pec minor tightness.

Data point 14—Shoulder flexion external rotation (modified apley's shoulder test)

Differential diagnosis: shoulder impingement, anterior translation of the scapula, ipsilateral neck pain, scapular dysfunction.

Data point 15—Cervical rotation (left and right)

Data point 16—Neck rotation

Differential diagnosis: Cervical herniated disc, TOS, plexus entrapment, previous head trauma.

Data point 17—Wrist extension

Differential diagnosis: flexor mass injury, carpal tunnel/nerve entrapment.

Data point 18—Wrist supination

Differential diagnosis: Flexor mass injury, carpal tunnel syndrome.

Data point 19—Wrist pronation

Differential diagnosis: contralateral supinator (deep branch of the radial nerve), with flexion, stretch of superficial branch of the radial nerve, compression of the median nerve.

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A goniometer device comprising:
a smartphone comprising:
an accelerometer that is configured to output a respective angular orientation value for each of three different axes;
a database storing (i) data indicating a sequence of angular measurements for a specific biomechanical exam that are to be obtained in a particular order, and, (ii) for each angular measurement, data indicating a subset of the three different axes that are relevant to generate the angular measurement when the goniometer device is removably placed and is held against a patient, wherein different angular measurements of the sequence have different axes that are indicated as relevant;
an input unit for receiving a user input that indicates that the goniometer device has been removably placed on the patient and is being held in a starting position of a given angular measurement and a user input that indicates that the goniometer device has been removably placed on the patient and is being held in an ending position of the given angular measurement;
a display unit of the smartphone for outputting calculated angular measurement values for each angular measurement of the sequence; and
one or more computer processors that are configured to perform operations comprising:
for each angular measurement of the sequence and in the particular order and until all measurements of the sequence have been obtained:

providing, for display to the user on the display unit, placement guidance illustrating how to hold the goniometer device by hand against the patient to take the angular measurement;

receiving the user input that indicates that the goniometer device has been removably placed by hand on the patient and is being held by hand in the starting position for the angular measurement;

obtaining, for the starting position, a respective angular orientation value for each of the three different axes;

receiving the user input that indicates that the goniometer device has been removably placed by hand on the patient and is being held by hand in the ending position of the angular measurement;

obtaining, for the ending position, a respective angular orientation value for each of the three different axes;

generating processed angular orientation values for the starting position and for the ending position based on the data indicating the subset of the three different axes that are relevant to the angular measurement, the processed angular orientation values excluding one or more angular orientation values of the starting position and the ending position for axes that are not in the subset;

calculating an angular measurement value for the angular measurement based on the processed angular orientation values for the starting position and for the ending position; and providing, for display on the display unit, the calculated angular measurement value and an instruction to move the goniometer device.

2. The goniometer device of claim 1, wherein the calculated angular measurement value is calculated using only the angular orientation values that are pre-associated in the database with a particular angular measurement of the sequence.

3. The goniometer device of claim 1, wherein the sequence of angular measurements are measurements that are specific to a Movement Analytics Performance System (MAPS).

4. The goniometer device of claim 1, comprising predicting a musculoskeletal injury using the sequence of angular measurements.

5. The goniometer device of claim 1, wherein the excluded one or more angular orientation values are identifiable to the goniometer device before the input unit receives the user input that indicates that the goniometer device is in the starting position.

6. The goniometer device of claim 1, wherein the display unit is further configured to output warnings to the user when, while a measurement is occurring, the goniometer tilts more than a threshold angle toward one or more of the axes that are not in the subset.

7. The goniometer device of claim 1, wherein, for each angular measurement, the subset of the three different axes are indicated without prompting a user to identify the subset.

8. A computer-implemented method comprising:

by a goniometer device that comprises a smartphone that comprises:
  an accelerometer that is configured to output a respective angular orientation value for each of three different axes;
  a database storing (i) data indicating a sequence of angular measurements for a specific biomechanical exam that are to be obtained in a particular order, and, (ii) for each angular measurement, data indicating a subset of the three different axes that are relevant to calculate the angular measurement when the goniometer device is removably placed and is held against a patient, wherein different angular measurements of the sequence have different axes that are indicated as relevant;
  an input unit for receiving a user input that indicates that the goniometer device has been removably placed on the patient and is being held in a starting position of a given angular measurement and a user input that indicates that the goniometer device has been removably placed on the patient and is being held in an ending position of the given angular measurement;
  a display unit of the smartphone for outputting calculated angular measurement values for each angular measurement of the sequence; and
  one or more computer processors that are configured to perform operations comprising:
    for each angular measurement of the sequence and in the particular order and until all measurements of the sequence have been obtained:
      providing, for display to the user on the display unit, placement guidance illustrating how to hold the goniometer device by hand against the patient to take the angular measurement;
      receiving the user input that indicates that the goniometer device has been removably placed by hand on the patient and is being held by hand in the starting position for the angular measurement;
      obtaining, for the starting position, a respective angular orientation value for each of the three different axes;
      receiving the user input that indicates that the goniometer device has been removably placed by hand on the patient and is being held by hand in the ending position of the angular measurement;
      obtaining, for the ending position, a respective angular orientation value for each of the three different axes;
      generating processed angular orientation values for the starting position and for the ending position based on the data indicating the subset of the three different axes that are relevant to the angular measurement, the processed angular orientation values excluding one or more angular orientation values of the starting position and the ending position for axes that are not in the subset;
      calculating an angular measurement value for the angular measurement based on the processed angular orientation values for the starting position and for the ending position; and
      providing, for display on the display unit, the calculated angular measurement value and an instruction to move the goniometer device.

9. The method of claim 1, wherein the calculated angular measurement value is calculated using only the angular orientation values that are pre-associated in the database with a particular angular measurement of the sequence.

10. The method of claim 8, wherein the sequence of angular measurements are measurements that are specific to a Movement Analytics Performance System (MAPS).

11. The method of claim 8, comprising predicting a musculoskeletal injury using the sequence of angular measurements.

12. The method of claim 8, wherein the excluded one or more angular orientation values are identifiable to the goniometer device before the input unit receives the user input that indicates that the goniometer device is in the starting position.

13. The method of claim 8, wherein the display unit is further configured to output warnings to the user when, while a measurement is occurring, the goniometer tilts more than a threshold angle toward one or more of the axes that are not in the subset.

14. The method of claim 8, wherein, for each angular measurement, the subset of the three different axes are indicated without prompting a user to identify the subset.

15. A non-transitory, computer-readable medium storing one or more instructions executable by a computer system to perform operations comprising:
- by a goniometer device that comprises a smartphone that comprises:
  - an accelerometer that is configured to output a respective angular orientation value for each of three different axes;
  - a database storing (i) data indicating a sequence of angular measurements for a specific biomechanical exam that are to be obtained in a particular order, and, (ii) for each angular measurement, data indicating a subset of the three different axes that are relevant to calculate the angular measurement when the goniometer device is removably placed and is held against a patient, wherein different angular measurements of the sequence have different axes that are indicated as relevant;
  - an input unit for receiving a user input that indicates that the goniometer device has been removably placed on the patient and is being held in a starting position of a given angular measurement and a user input that indicates that the goniometer device has been removably placed on the patient and is being held in an ending position of the given angular measurement; and
  - a display unit for outputting calculated angular measurement values for each angular measurement of the sequence;
- for each angular measurement of the sequence and in the particular order and until all measurements of the sequence have been obtained:
  - providing, for display to the user on the display unit, placement guidance illustrating how to hold the goniometer device by hand against the patient to take the angular measurement;
  - receiving the user input that indicates that the goniometer device has been removably placed by hand on the patient and is being held by hand in the starting position for the angular measurement;
  - obtaining, for the starting position, a respective angular orientation value for each of the three different axes;
  - receiving the user input that indicates that the goniometer device has been removably placed by hand on the patient and is being held by hand in the ending position of the angular measurement;
  - obtaining, for the ending position, a respective angular orientation value for each of the three different axes;
  - generating processed angular orientation values for the starting position and for the ending position based on the data indicating the subset of the three different axes that are relevant to the angular measurement, the processed angular orientation values excluding one or more angular orientation values of the starting position and the ending position for axes that are not in the subset;
  - calculating an angular measurement value for the angular measurement based on the processed angular orientation values for the starting position and for the ending position; and
  - providing, for display on the display unit, the calculated angular measurement value and an instruction to move the goniometer device.

16. The medium of claim 15, wherein the calculated angular measurement value is calculated using only the angular orientation values that are pre-associated in the database with a particular angular measurement of the sequence.

17. The medium of claim 15, wherein the sequence of angular measurements are measurements that are specific to a Movement Analytics Performance System (MAPS).

18. The medium of claim 15, comprising predicting a musculoskeletal injury using the sequence of angular measurements.

19. The medium of claim 15, wherein the excluded one or more angular orientation values are identifiable to the goniometer device before the input unit receives the user input that indicates that the goniometer device is in the starting position.

20. The medium of claim 15, wherein the display unit is further configured to output warnings to the user when, while a measurement is occurring, the goniometer tilts more than a threshold angle toward one or more of the axes that are not in the subset.

21. The medium of claim 15, wherein, for each angular measurement, the subset of the three different axes are indicated without prompting a user to identify the subset.

* * * * *